US006203560B1

(12) United States Patent
Blach et al.

(10) Patent No.: US 6,203,560 B1
(45) Date of Patent: *Mar. 20, 2001

(54) NASAL SUPPORT DEVICE FOR DOMESTIC MAMMALS AND METHOD

(75) Inventors: Edward L. Blach, Roswell, NM (US); James R. Chiapetta, Eagan, MN (US)

(73) Assignee: WinEase LLC, Eagan, MN (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/375,816

(22) Filed: Aug. 17, 1999

Related U.S. Application Data

(63) Continuation of application No. 09/250,658, filed on Feb. 16, 1999, now Pat. No. 6,017,357, which is a continuation of application No. 08/843,741, filed on Apr. 21, 1997, now Pat. No. 5,913,873.

(51) Int. Cl.[7] .............................. A61M 29/00
(52) U.S. Cl. .............................. 606/199; 128/200.24
(58) Field of Search .............................. 606/199, 201, 606/204.45; 128/200.24; 602/41, 74, 902

(56) References Cited

U.S. PATENT DOCUMENTS

| | | | | |
|---|---|---|---|---|
| Re. 35,408 | | 12/1996 | Petruson . | |
| 1,232,956 | | 7/1917 | Mooney . | |
| 5,476,091 | | 12/1995 | Johnson . | |
| 5,533,499 | * | 7/1996 | Johnson | 128/200.24 |
| 5,533,503 | | 7/1996 | Doubek et al. . | |
| 5,546,929 | | 8/1996 | Muchin . | |
| 5,549,103 | | 8/1996 | Johnson . | |
| 5,553,605 | | 9/1996 | Muchin . | |
| 5,611,333 | * | 3/1997 | Johnson | 128/200.24 |
| 5,611,334 | * | 3/1997 | Muchin | 128/200.24 |
| 5,653,224 | * | 8/1997 | Johnson | 128/200.24 |
| 5,669,377 | | 9/1997 | Fenn . | |
| 5,706,800 | * | 1/1998 | Cronk et al. | 128/200.24 |
| 5,718,224 | | 2/1998 | Muchin . | |
| 5,755,232 | | 5/1998 | Kalt . | |
| 5,765,548 | * | 6/1998 | Perry | 128/200.24 |
| 5,817,039 | * | 10/1998 | Raunig | 602/5 |
| 5,890,486 | | 4/1999 | Mitra et al. . | |
| 5,913,873 | * | 6/1999 | Blach et al. | 606/199 |
| 5,947,119 | | 9/1999 | Reznick . | |
| 5,954,049 | * | 9/1999 | Foley et al. | 128/200.24 |
| 5,976,173 | | 11/1999 | Berke . | |

FOREIGN PATENT DOCUMENTS

| | | | | |
|---|---|---|---|---|
| 65890/96 | | 4/1998 | (AU) . | |
| 289561 | * | 10/1985 | (ES) | 128/200.24 |
| 768488 | | 2/1957 | (GB) . | |
| 2313313 | | 11/1997 | (GB) . | |
| WO 92/22340 | | 12/1992 | (WO) . | |
| WO 94/23675 | | 10/1994 | (WO) . | |
| WO 97/02793 | | 1/1997 | (WO) . | |
| WO 98/12998 | | 4/1998 | (WO) . | |

OTHER PUBLICATIONS

Kev's World Cartoon (Exhibit 1).

(List continued on next page.)

*Primary Examiner*—Glenn K. Dawson
(74) *Attorney, Agent, or Firm*—Merchant & Gould. P.C.

(57) ABSTRACT

The present disclosure provides a device and method for facilitating air flow in the nasal passage of a domestic animal. The device is a nasal support device useful for facilitating air flow during rest, physical exertion, respiratory ailment, etc. In one embodiment the nasal support device secures to the nose of a domestic animal to support the unsupported lateral vestibular walls of the nasal passages by lifting or stinting.

18 Claims, 7 Drawing Sheets

OTHER PUBLICATIONS

Declaration of James R. Chiapetta re: Kev's World Cartoon.
Art et al., "Effect of exercise on the partitioning of equine respiratory resistance," *Equine Vet J* 20(4):268–273 (Jul. 1988).
Art et al., "Mechanics of breathing during strenuous exercise in thoroughbred horses," *Respir Physiol* 82:279–294 (1990).
Di Somma et al., "Nasal dilator strips increase maximum inspiratory flow via nasal wall stabilization," *The Laryngoscope* 109:780–784 (May 1999).
Erickson, "Exercise induced pulmonary haemorrhage," *Proceedings of the Fourth International Conference on Equine Exercise Physiology*, (Jul. 11–16, 1994) in *Equine Vet J Suppl* 18:476–478 (1995).
Erickson et al., "Pulmonary artery, aortic and oesophageal pressure changes during high intensity treadmill exercise in the horse: a possible relation to exercise–induced pulmonary haemorrhage," *Equine Vet J Suppl* 9:47–52 (1990).
Erickson et al., "What Causes Racehorse Lungs to Bleed?," *The Quarter Racing J.,* 52–57 (May 1995).
Fedde et al., "Increase in blood viscosity in the sprinting horse: can it account for the high pulmonary arterial pressure?," *Equine Vet J.,* 30(4):329–334 (1998).
Foerner, "The Diagnosis and Correction of False Nostril Noises," *AAEP Proceedings*, pp. 315–327 (1967).
Funkquist et al., "Studies on the intratracheal pressure in the exercising horse," *J. Vet. Med A,* 35:424–441 (1988).
Gillespie, "The role of respiratory system during exertion," *J S Afr Vet Assoc* 45(4):305–309 (1974).
Goetz et al., "Pressures in the right side of the heart and esophagus (pleura) in ponies during exercise before and after furosemide administration," *Am J Vet Res* 47(2):270–277 (Feb. 1986).
Guillette, "Use of Nasal Valve Stent with Anterior Rhynomanometry to Quantitate Nasal Valve Obstruction;" *Ann. Otol. Rhinol. Laryngol,* 99:175–178 (1990).
Haight et al., "The Site and Function of the Nasal Valve," *Laryngescope* 93:49–55 (Jan. 1983).
Hinchcliff, "Effects of furosemide on athletic performance and exercise–induced pulmonary hemorrhage in horses," *J Am. Vet Med. Assoc.*, 215(5):630–635 (Sep. 1999).
Jackson et al., "Effects of airway obstruction on transmural pulmonary artery pressure in exercise horses," *Am J Vet Res* 58(8):897–903 (Aug. 1997).
Johnson et al., "Modelling exercise–induced pulmonary hemorrhage in racing thoroughbreds," *Frontiers Med Biol Eng* 4(4):271–289 (1992).
Jones et al., "The nasal valve: a physiological and clinical study," *J. of Laryngol. and Oto.*, 102:1089–1094 (Dec. 1988).
Lekeux et al. "The respiratory system: anatomy, physiology, and adaptations to exercise and training," *The Athletic Horse,* DR Hodgson and RJ Rose (eds), WB Saunders (1994).
Manohar, "Furosemide attenuates the exercise–induced increase in pulmonary artery wedge pressure in horses," *Am. J. Vet. Res.*, 54(6):952–958 (Jun. 1993).
Manohar, "Furosemide attenuates the exercise–induced rise in pulmonary capillary blood pressure in horses," *Equine Vet. J.,* 26(1):51–54 (1994).
McKane et al., "Equine bronchoalveolar lavage cytology: survey of Thoroughbred racehorses in training," *Aust. Vet. J.,* 70(11):401–404 (Nov. 1993).*
Meyer et al., "Quantification of exercise–induced pulmonary haemorrhage with bronchoalveolar lavage," *Equine Vet. J.,* 30(4):284–288 (1998).*
Olsen et al., "Influence of furosemide on hemodynamic responses during exercise in horses," *Am. J. Vet. Res.,* 53(5):742–747 (May 1992).*
Robinson et al., "Pathophysiology of airway obstruction in horses: A Review," *J Am Vet Med Assoc*, 172(3):299–303 (Feb. 1, 1978).*
Roithmann et al., "Acoustic Rhinometric Assessment of the Nasal Valve," *American Journal of Rhinology,* 11(5):379–402 (1997).*
Sinha et al., "Pleural pressure changes during exercise do not affect measurement of mean vascular pressures," *Equine Vet J Suppl.,* 18:95–98 (1995).*
Whitwell et al., "Collection and evaluation of tracheobronchial washes in the horse," *Equine Vet. J.,* 16(6):499–508 (1994).*

* cited by examiner

NASAL SUPPORT DEVICE FOR DOMESTIC MAMMALS AND METHOD

The present application is a continuation application of U.S. Ser. No. 09/250,658, filed Feb. 16, 1999, now U.S. Pat. No. 6,017,357, which is a continuation application of U.S. Ser. No. 08/843,741, filed Apr. 21, 1997, now U.S. Pat. No. 5,913,873, which applications are incorporated herein by reference.

FIELD OF THE INVENTION

The present invention is directed to facilitating the inspiration of air in a domestic mammal. Specifically, the invention provides a device and method for supporting the size of the nasal passages of a domestic animal.

BACKGROUND OF THE INVENTION

Portions of the following discussion of the nasal anatomy of domestic mammals are excerpted from R. Nickel et al., *The Viscera of Domestic Animals*, (2nd revised ed.), Springer-Verlag, New York, Hiedelberg, Berlin (1979), pp. 211–221. This is an excellent text on the comparative visceral anatomy of domestic mammals. As used herein, the terms "mammal" and "animal" are synonymous and refer to non-human mammals.

Unlike the human nose that projects distinctly from the face, in domestic animals, the nose is incorporated into the face and forms the large dorsal and lateral areas rostral to the eyes. The nostrils at the apex of the nose are the entry to the respiratory system of domestic mammals. Once passing through the nostrils, inspired air moves into the nasal cavities and continues through the nasopharynx, larynx, trachea and lungs.

At the apical entrance to the nose the nostrils are partitioned by the nasal septum to divide the nasal cavity into right and left halves. The caudal portion of the septum is bony, while rostrally the septum consists of cartilage and becomes progressively more flexible towards the apex.

The wall of the nose consists of skin externally and a middle supporting layer of bone caudally and cartilage rostrally. The nasal cavity is lined by a mucous membrane. The rostral bones forming the wall of the nose include the nasal, maxillary and incisive bones. The free borders of the nasal and incisive bone provide attachment for the cartilages which support the nostrils. The supporting bones and cartilages of the nose are associated with the nasal muscles that regulate the width of the nostrils.

The dorsal and ventral lateral nasal cartilages are formed by the widening of the rostral part of the nasal septum along its dorsal and ventral margins. In the horse, the ventral lateral nasal cartilage is small and may be absent. In many domestic animals, there is no lateral support for the soft tissue over the rostral nasal passage caudal to the nostril.

A further difference in the anatomical support of the nasal passages of the horse is the presence of alar cartilages in the formation of the nasal cartilages. The alar cartilages consist of a ventral comu and a dorsal lamina and support the nostrils dorsally, medially and ventrally. The lamina of the alar cartilage and the medial accessory cartilage support the nasal diverticulum, a blind pouch in the dorsal aspect of the nostril.

The muscles of the nose and upper lip act to dilate the nostrils. This is particularly noticeable during labored breathing. In the horse, these muscles are well developed and can operate to cause the normally semilunar nostrils to become circular.

The dorsal lateral area of the rostral nasal cavity that is caudal to the alar cartilages in the nostrils of the horse includes a region of unsupported soft tissue which can be drawn into the nasal cavity during inspiration of air into the nasal passages. When the skin is drawn in, it can narrow the nasal cavity and reduce the area for the intake of air, thus reducing the air movement into the nasal passages and ultimately to the lungs where the oxygen is transferred in the pulmonary aveoli. The physiological effects of reduced oxygen transfer at rest and during physical exertion are known.

Devices for dilating the outer wall tissue of the nasal passages in humans have been described in, for example, U.S. Pat. Nos. 5,533,503; 5,546,929; 5,553,605; and RE 35,408. Most of these devices, however, do not address the unique aspects and structural problems of supporting the nasal tissues of non-human mammals, especially large performance mammals such as the horse and camel.

Accordingly, there is a need to reduce the detrimental effects of reduced air intake, or to enhance the physiological benefit of increased air intake, during physical exertion of domestic mammals. Specifically, there is a need to increase, or reduce the decrease of, nasal passage narrowing that can occur during breathing in domestic mammals, especially performance animals such as the horse, camel, and dog.

SUMMARY OF THE INVENTION

The present invention provides a device and method for supporting the unsupported nasal tissues of a domestic animal. The invention addresses the structural and physiological characteristics unique to the nose of an animal.

In one embodiment the invention provides a nasal support device (NSD) for securing to the nose of a domestic animal. The NSD provides support to the right and left lateral vestibular walls of a domestic animal. The device includes a support layer and a right and left side piece which when secured to the nose of the animal are positioned to provide structural support to the right and left vestibular walls. The side pieces of the device meet at the midline region of the device. When the NSD is secured to a domestic animal according to the invention, the midline region straddles the left and right nasal bones of the animal. The side pieces and midline region of an NSD each have a rostral end, a caudal end and a rostral-poll dimension. In one embodiment, the rostral-poll dimension of the midline region is at least as great as either of the rostral-poll dimensions of the side pieces. In an alternative embodiment, the rostral-poll dimension of the midline region is greater than either of the rostral-poll dimensions of the side pieces. In some embodiments, the rostral end of the NSD can extend rostrally between the nostrils in the form of a "tongue" to provide externalizing support to the soft tissues between the nostrils.

AN NSD configured according the invention can be used on many different animals. In one embodiment an NSD is sized to fit a member of the Equidae family, including the domestic horse. The device is suitable for adult and young animals. In general, the functional aspects of a device of the invention can be configured and sized to fit the nose of, for example, a dog, human, horse, camel, etc.

An NSD includes a support layer and preferably an engaging layer and a surface layer. The support layer of an NSD can include one or more lift members to support the vestibular wall. The lift members can traverse the nose and extend ventrally along the vestibular wall, or beyond the ventral border of the vestibular wall to the lateral aspect of the incisive bone.

Preferably. an NSD includes an engaging layer providing for securing the NSD to the nose of an animal. Preferably, an NSD includes a surface layer and in some embodiments, a pad layer.

The invention further provides a method for supporting a right and left vestibular free wall of a domestic animal. According to the method, a device for supporting the first and second vestibular free wall is secured to the nose of the animal. In one embodiment, the device is an NSD according to the invention.

The method of the invention provides for facilitating air flow in the nasal passages of a domestic animal. The method of the invention is particularly advantageous for use in the horse and camel and is beneficial both for facilitating athletic performance or for treating disease, for example, as a palliative therapy for upper respiratory disease in an adult or young animal.

A device and method according to the invention can be used on an animal that is running freely in a pasture, or wearing saddlery, harnesses or other equipment that can be attached to the nose of the animal.

BRIEF DESCRIPTION OT THE DRAWINGS

FIG. 1*a* is a top view of one configuration of an embodiment of an NSD which incorporates the functional aspects of the invention.

FIG. 1*b* is a top view of a second configuration of an embodiment of an NSD which incorporates the functional aspects of the invention.

FIG. 1*c* is a top view of a third configuration of an embodiment of an NSD which incorporates the functional aspects of the invention.

FIG. 1*d* is a top view of a fourth configuration of an embodiment of an NSD which incorporates the functional aspects of the invention.

FIG. 1*e* is a top view of a fifth configuration of an embodiment of an NSD which incorporates the functional aspects of the invention.

FIG. 1*f* is a top view of a sixth configuration of an embodiment of an NSD which incorporates the functional aspects of the invention.

FIG. 1*g* is a top view of a seventh configuration of an embodiment of an NSD which incorporates the functional aspects of the invention.

DETAILED DESCRIPTION OF THE INVENTION

Figure 1A:
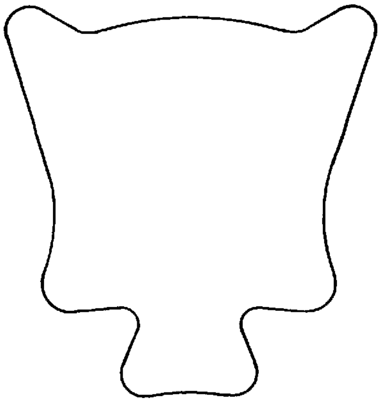
Figure 1D:
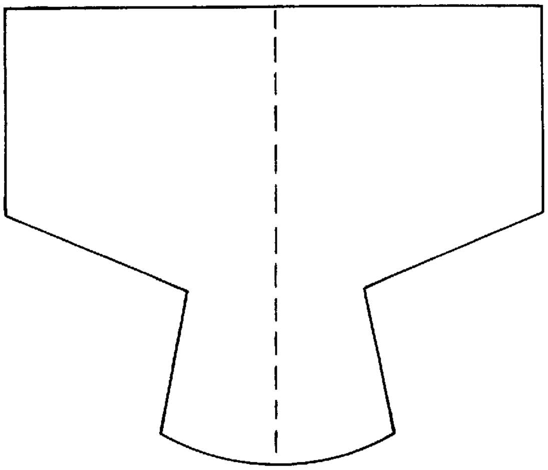
Figure 1B:
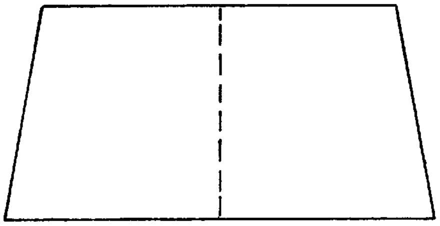
Figure 1E:
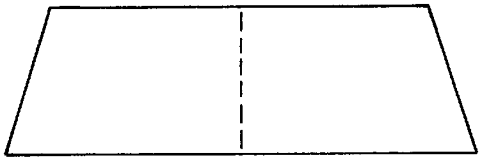

The invention is directed to devices and methods to support soft tissue at the rostral aspect of the nasal cavity of domestic mammals. As used herein, domestic mammals include most non-human production and performance animals having a nose incorporated into the face, rather than projecting therefrom, that can benefit from a device according to the invention. Such mammals include, for example, dogs, sheep, goats, cattle, horses, camels, llamas, etc. A device according to the invention can be particularly useful for an equine, that is, members of the Equidae family including horses, donkeys, mules, zebras etc.; camels, or other animals which are used for work. "Work" includes activities such as pulling, driving, racing (flat, steeple, barrel, cutting, etc.), eventing, hunting, jumping, rodeoing, trail riding, endurance riding, etc. In general, the device can be used anytime it is desired to facilitate or enhance air intake through the nasal passages. This includes use in the treatment of respiratory ailments in adult or young animals such as foals or calves.

For the present disclosure, the devices and methods of the invention are directed to supporting the unsupported region of the "vestibule" in the rostral nasal cavity. The disclosure provides "nasal support devices" (NSD) and methods which are suitable for securing to an animal nose and supporting the associated external soft tissues.

As used herein, the term rostral refers to that aspect of the nose or other anatomical structure closest to the apex of the nose. Caudal refers to that aspect of the nose closest to the poll or caudal aspect of the head relative to the apex. The "vestibule" refers to the rostral aspect of the nasal cavity that is defined by the nostrils rostrally, the incisive bone ventrally, the nasal bone dorsally, the caudal intersection of the incisive and nasal bones caudally, and the nasal septum medially. Thus, supported regions of the vestibule are supported by bone or cartilage.

The "unsupported" region of the vestibule is also referred to as the "lateral (free) wall" of the vestibule. The lateral wall of the vestibule is the unsupported soft tissue defined by the nostrils rostrally, the lateral free border of the nasal bone dorsally, the dorsal free border of the incisive bone ventrally, and the intersection of the nasal and incisive bone caudally. In the horse, the dorsal border of the unsupported region can include the dorsal lateral nasal cartilage and, in some species, the ventral border can include the ventral lateral nasal cartilage. Herein, "soft tissue" has its general meaning including skin, muscle, fat, connective tissue and associated integumentary structures.

In general, the nasal anatomy of "soft" muzzled mammals such as the horse and camel give rise to unique mechanical problems in supporting the surrounding soft tissues. For example, in the horse, the alar cartilages that are attached at the rostral border of the nasal septum supports the alar fold which gives rise to the blind cutaneous pouch referred to as the "false" nostril. Providing structural support for the vestibule of the horse preferably includes support of the alar fold. A suitable support device according to the invention, preferably causes minimal irritation to the skin or other anatomic structures of the animal when in use.

Another factor considered in providing an NSD for support of the vestibule of a horse or camel is the equipment including saddlery or harnesses worn by the animal when working. Generally, "saddlery" refers to bits, bridles, martingales, muzzles, headcollars, saddles and other equipment used with a riding animal. "Harness" refers to equipment used with a driving animal. AN NSD of the invention, preferably does not interfere with the functioning of saddlery or harnesses and the saddlery or harnesses preferably do riot interfere with the functioning of the NSD.

It should be noted that an NSD according to the present invention need only engage the lateral free wall of the vestibule. The NSD does not need to engage the nostril. In the horse, for example, the muscles of the nose and upper lip provide sufficient "flaring" of the nostril during labored breathing. Generally, the nostril of the horse can expand to provide an opening to the nasal passage that is greater than the expandable size of the vestibular free wall.

Some exemplary embodiments of a device of the invention and its components are described below. Throughout the specification guidance is provided by examples of representative groups, the groups are not meant to be limiting.

The configuration of a nasal support device is determined by the configuration of the tissue to be supported and the amount of support needed Typically, the unique nasal anatomy of domestic animals necessitates configurations, arrangements or dimensions which are different than that required for a human nose. Some human nasal dilators such as disclosed in U.S. Pat. Nos. 5,533,503; 5,546,929; 5,553,605 and RE 35,408 have first and second enlarged ends joined by a narrow elongate intermediate section, giving a "dumbell" appearance. An NSD for domestic animals as disclosed herein, does not use such a tripartite arrangement.

In a typical embodiment, an NSD disclosed herein for a domestic animal provides support to the right and left lateral vestibular walls of the animal. Generally, the device includes a support layer having a right and left side piece which when secured to the nose of the animal are positioned to provide structural support to the right and left lateral vestibular walls. The "right and left" side pieces can also be referred to as "first and second" or "second and first" side pieces. The NSD is generally bilaterally symmetrical without a narrow elongate intermediate section between the side pieces. The side pieces of the device meet at about the midline of a midline region of the device. When the NSD is secured to a domestic animal, the intersection of the right and left side pieces at the midline region substantially straddles the left and right nasal bones of the animal.

The side pieces and the midline region of an NSD each have a rostral end, a caudal end and a rostral-poll dimension. Because of the size and related anatomy of the surface area of the vestibular free wall of, for example a horse, to provide sufficient support to benefit the animal, the rostral-poll dimension of the midline region of an NSD of the invention can be substantially equal to or greater than the rostral poll dimension of the side pieces that engage the vestibular free wall. Hence, in one embodiment, the rostral-poll dimension of the midline region can be at least as great as the rostral-poll dimension of either of the side pieces. In an alternative embodiment, the rostral-poll dimension of the midline region is greater than the rostral-poll dimension of the right or left side piece. It is foreseen, however, that although an NSD of the invention configured for use on an animal nose, the unique configuration disclosed herein could provide an advantageous improvement in the lift effect of a dilator for a human nose.

In some embodiments, the rostral end of the NSD at or near the midline region extends to the apex of the muzzle between the nostrils and is referred to as a "tongue". This embodiment can provide externalizing lift support to the most rostral aspect of the cartilaginous nasal septum between the nostrils.

The structural configuration and arrangement of an NSD can vary in some aspect(s) and still maintain the mechanical functioning of a device according to the invention. Personalization of the design appearance of the invention can reflect aesthetics, personal tastes, racing colors, etc. The overall appearance of the embodiments illustrated in the present application are not exhaustive of those which are within the scope of the invention. Examples of a few general configurations which are ornamental but maintain some or all of the functional aspects of the invention are shown in the top plan views of FIGS. 1*a–g*, and 5–7. Generally, the bottom plan configuration of an NSD is substantially identical to the top plan configuration shown. The side plan view of an NSD generally is substantially void of ornamental features.

As used herein, the term "support" refers to reducing the amount of narrowing of the nasal passage that can occur during inspiration or expiration of domestic animals. Accordingly, "support" includes some drawing in of the vestibular free wall at the rostral nasal passage during inspiration, but less than that which would occur without a device of the invention. "Support" also includes maintaining the position of external soft tissue over the rostral nasal passage in a neutral position. As used herein, "neutral" refers to a state where the unsupported vestibular tissues are neither drawn into the nasal cavity nor protruding externally. In some arrangements, "support" also includes maintaining the vestibular free wall in a "distended" outward position relative to the neutral position.

Because of the different nasal anatomy present in domestic animals than in humans, the configuration of a suitable NSD for animals takes into account the configuration and size of the vestibular free wall and the anatomical structures defining its borders. Moreover, in most large domestic animals, the structural support necessary to support the lateral free wall also takes into account the weight of the tissue supported and the proper leveraging for distributing the weight supported without causing pressure sores or other irritation to surrounding tissues.

The size of a device of the invention can vary. Appropriately sized devices will typically correspond with muzzle size which can vary with the body size, breed, age, and sex, of the animal. It is foreseen that smaller sized NSDs for young animals, such as calves and foals can be beneficial in treating diseases including, for example, upper respiratory ailments. In some presently preferred embodiments, the rostral-poll midline dimension of an NSD for an average sized adult horse is about 5 to 18 cm, and the right and left side piece rostral-poll dimension is about 5 to 8 cm. However, larger and smaller sizes may be used.

The transverse dimension of an NSD can also vary. The "transverse dimension" is defined as the length of the device from the peripheral edge of one side of the device to the peripheral edge of the other side of the device. The transverse dimension can vary in a single device depending if measured, for example, along the caudal edge, the rostral edge, the narrowest part or the widest part. In one embodiment of an NSD for an average size horse, the transverse dimension at the widest part can be about 10 cm to about 17 cm.

Generally, an NSD according to the invention includes at least a "support layer" which provides the majority of the support for the vestibular wall. The device also preferably includes an "engaging" layer for attaching the device to a domestic animal. In some embodiments a "surface layer" can be present to cover the side of the support layer that is away from the nose of the animal when the device is secured to the nose of an animal. Some embodiments can also include one or more "pad layers" which can help reduce the chance of pressure sores caused by the device.

According to the invention, the support layer provides the majority of the support for the vestibular free wall of the nasal passage. Generally, support is provided in the support layer through the use of one or more "lift members." As used herein a "lift member" can be prepared from any type of resilient material which provides the desired support to the vestibular free wall. Examples of suitable materials for a lift member include thermoplastic resins, thermoset resins, shape memory metals or alloys, etc. The lift members can be an open mesh or solid material. Of the thermoplastic resins, a variety of thermoplastic films can be used, including, for example, poly (acrylonitrile-co-butadiene-co-styrene) polymers, acrylic polymers such as the polymethylmethacrylate, poly-n-butyl acrylate, poly (ethylene-co-acrylic acid), poly(ethylene-co-methacrylate), etc.; fluoropolymers including polytetrafluoroethylene (teflon), poly(ethylene-co-tetrafluoroethylene) copolymers, (tetrafluoroethylene-co- propylene) copolymers, polyvinyl fluoride polymers, etc., polyamides such as nylon 6, nylon 6,6, etc.; polycarbonates; polyesters such as poly(ethylene-co-terephthalate), poly(ethylene-co-1,4-naphthalene dicarboxylate), poly(butylene-co-terephthalate); polyimide materials; polyethylene materials including low density polyethylene; linear low density polyethylene, high density polyethylene, high molecular weight high density polyethylene, etc.; polypropylene, biaxially oriented polypropylene; polystyrene, biaxially oriented polystyrene; vinyl films including polyvinyl chloride. (vinyl chloride-co-vinyl acetate) copolymers, polyvinylidene chloride. polyvinyl alcohol, (vinyl chloride-co-vinylidene dichloride) copolymers, specialty films including polysulfone, polyphenylene sulfide, polyphenylene oxide, liquid crystal polyesters, polyether ketones, polyvinylbutyrl, etc. A preferred thermoplastic resin is a polyester such as MYLAR® available from DuPont Films, Wilmington Del.

Preferably, the lift members are a uniform thickness throughout their length and width. The thickness will typically be selected based on the support needed. Suitable thickness for a lift member prepared from MYLAR® for an adult large animal such as a horse is about 0.008 to about 0.020 inches. In one presently preferred embodiment, the thickness of a support member for an average size adult horse is about 0.014 inches.

The support layer can include one or more lift members. In one embodiment using a single lift member, the configuration of the peripheral edge of the lift member can define the external contours of the overall device. In other embodiments, two and preferably, three or more lift members are used. In this embodiment, a plurality of lift members can be arranged parallel along the transverse dimension of the device. Alternatively, a plurality of lift members can be oriented perpendicular to one another such that one or more lift members are oriented parallel to the transverse dimension of the device and one or more lift members are oriented parallel to the rostral-poll dimension of the device. In yet another embodiment, two or more lift members can be oriented in a substantially criss-cross arrangement to form an "X" shaped appearance in top plan view.

In some embodiments it is advantageous to provide lift members in a rostra-caudal direction. Lift members oriented in a rostral-caudal direction can be located in the side pieces to further support the externalizing force of the NSD. In addition, or alternatively, lift members can be oriented in a rostral caudal direction at or near the midline intersection of the first and second side pieces. This arrangement of the lift members is particularly advantageous for NSD embodiments which extend rostrally to form a "tongue" for support of the soft tissue between the nostrils.

The width, length and spacing of one or more lift members can vary based on the overall dimensions of the particular NSD. Preferably, the length dimension of a lift member is sufficient to traverse the midline of the animal's nose and extend to the right and left side pieces beyond the dorsal lateral nasal cartilages to support the right and left vestibular free walls. The members can vary in length to traverse some or all of the dorsal-ventral dimension of the vestibular free wall. In some embodiments, the lift members can extend beyond the ventral edge of the vestibular free wall to a point lateral to the incisive bone. Generally, the lift members provide a "lift" effect on the vestibular free wall to reduce the drawing of the vestibular free wall into the nasal passage during respiration. However, if the lift members extend beyond the ventral edge of the vestibular free wall to the lateral aspect of the incisive bone, the incisive bone can act as a "stint" to facilitate the reduction of the drawing in of the vestibular wall into the nasal cavity that is provided by the lift members. This may be particularly advantageous in large animals during significantly labored breathing. It is believed that an NSD of the invention can be particularly advantageous if fatigue induced muscle relaxation causes the vestibular wall to relax significantly, for example, near the end of a race.

When two or more lift members are used, the width of the lift members and the spacing between lift members are selected for the NSD to provide the desired support to the vestibular wall with sufficient flexibility to reduce the chance of irriation due to localized pressure at leveraging points on the animal's nose. In one embodiment of an NSD for an average size adult horse, the length of the lift members can be about 4–18 cm, the width can be about 0.2 to 2 cm and the spacing between lift members about 0.2 to 2 cm.

An NSD preferably includes an engaging layer. The engaging layer provides for securing a nasal support device (NSD) to the animal. Typically, the engaging layer can secure the NSD to the nose by use of an adhesive. Preferably, the adhesive is biocompatible and provides minimal or no contact irritation when applied to the external tissues of an animal. Suitable materials for the adhesive layer are known. One example of an adhesive containing material suitable as an engaging layer is No. 1509 double sided adhesive available from 3M Co., St. Paul, Minn.

The support layer can mount directly to the engaging layer. However, in some embodiments, it may be preferable to provide a "pad layer" between the engaging layer and support layer. The pad layer can be formed of any suitable known material. One preferred material is a polyester material that allows the skin of the vestibular wall beneath the device to breathe. An example of a suitable pad layer is the product SONTARA® (style nos. 8004, 8005, 8027 etc.) available from E.I. DuPont Nemours & Co., DuPont Nonwoven Division, Old Hickory, Tenn. SONTARA® is a nonwoven, spunlaced, breathable polyester fabric.

If no pad layer is used, the support layer can mount to the engaging layer. If the engaging layer is a double sided adhesive material, the lift members of the support layer can be adhered directly to the engaging layer. Alternatively, the lift members can be adhered to a non-adhesive side of the engaging layer, or to a nonadhesive pad layer using a double sided adhesive such as 3M No. 1509, 3M Inc., St. Paul, Minn.

In some preferred embodiments, an NSD can include a surface layer. The surface layer is the layer farthest from the soft tissues of the animal. The side of the surface layer closest to the soft tissue of the animal can include an adhesive to adhere the surface layer to the support layer, to the top side of the engaging layer that may be exposed between lift members, or to the pad layer if used. The surface layer can provide additional support to the vestibular wall and help maintain unity of the components of an NSD. A suitable surface material is preferably breathable and includes a biocompatible adhesive. An example of a material suitable as a surface layer is 3M No. 1533 available from 3M Inc., St. Paul, Minn. The surface layer can include an ornamental design color, pattern, logo etc. if desired. Alternatively, an ornamental veneer layer can be applied to the exposed surface of a surface layer or support layer or no surface layer is present.

The engaging layer, surface layer, or pad layer (if used) can closely follow the external contours defined by the support layer. Alternatively, the periphery of the engaging or other layers can extend beyond the contours defined by the support layer. In one preferred embodiment, extending the periphery of the engaging layer beyond the contours defined by the support layer can provide improved attachment of the NSD to the animal.

Generally, the overall thickness of the device is uniform. Some variation in thickness can occur due to differences in thickness of those regions of the device including the support members and those regions including spacing between support members. However, the thickness of the device preferably does not vary due to non-uniformity of the thickness of the lift members themselves.

DETAILED DESCRIPTION OF ILLUSTRATED EMBODIMENT

Some anatomical reference points and a few embodiments of an NSD according to the invention will be described in detail with reference to the drawings using the horse as an example. Like reference numerals represent like parts and assemblies throughout the several views. Reference to the drawings is not intended to limit the scope of the invention.

Figure 1C:
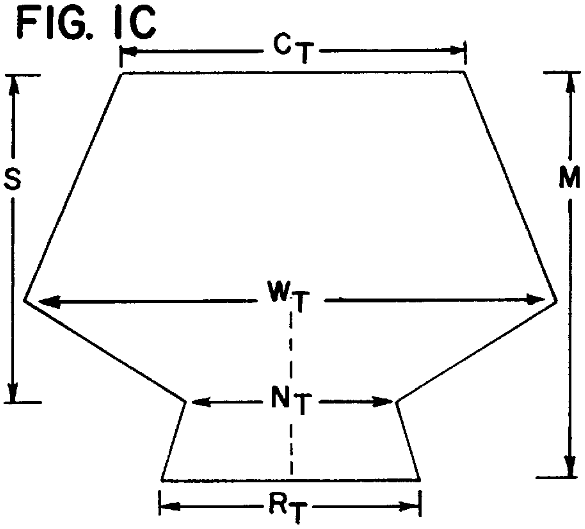
Figure 1F:
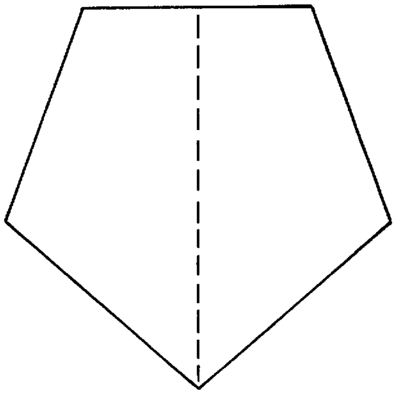
Figure 1G:
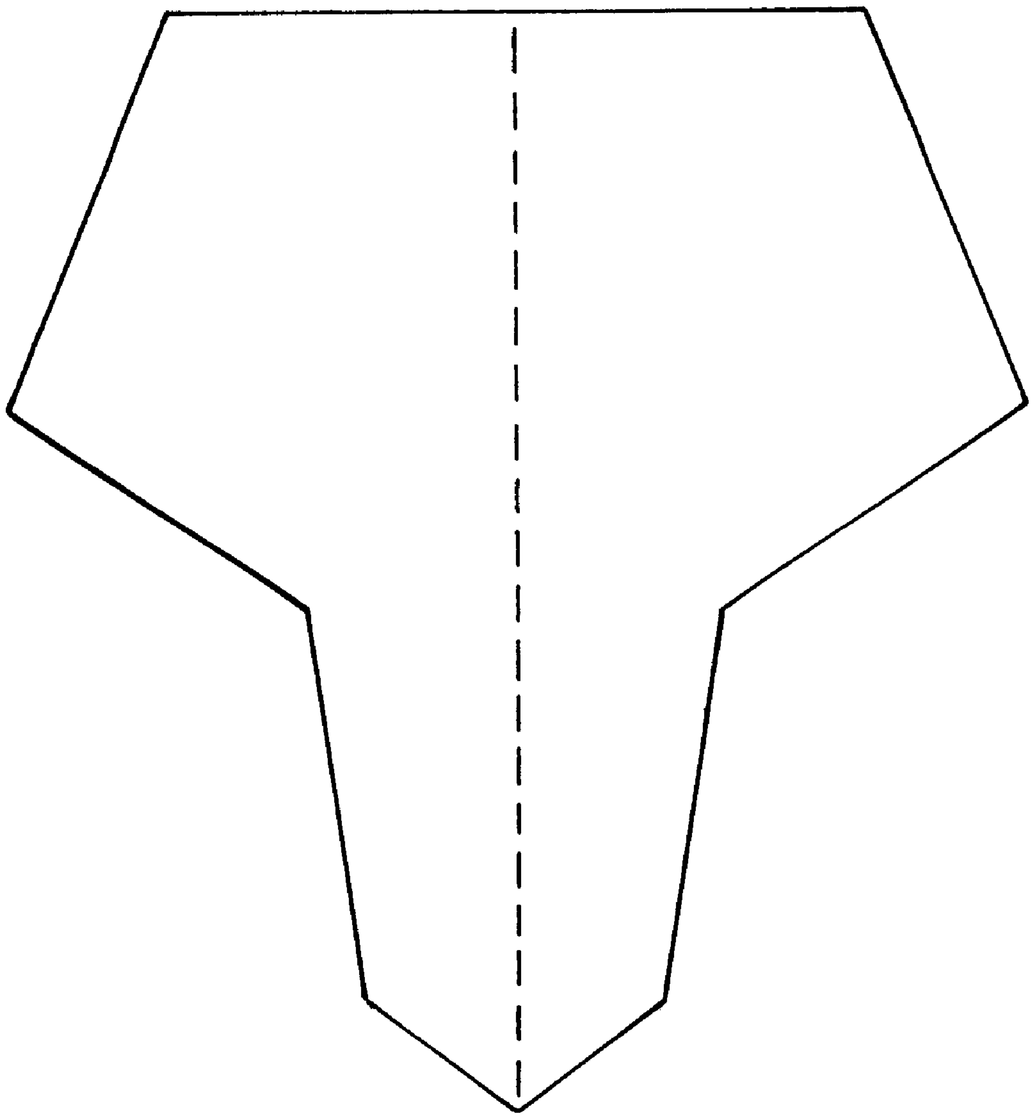

FIGS. 1*a–g* are each a top view of a configuration of an embodiment of an NSD which incorporates the functional aspects of the invention. The embodiments shown are exemplary and are not intended to limit the scope of configurations that incorporate the principles of the invention. FIG. 1*c* shows the several dimensions used to describe an NSD according to the invention wherein letters followed by a subscript "T" are the transverse dimensions including: $C_T$ is the caudal edge transverse dimension, $R_T$ is the rostral edge transverse dimension, $N_T$ is the narrowest part transverse dimension and $W_T$ is the widest part transverse dimension. S is the rostral-poll dimension of the side piece and M is the rostral poll dimension of the midline region.

Figure 2:
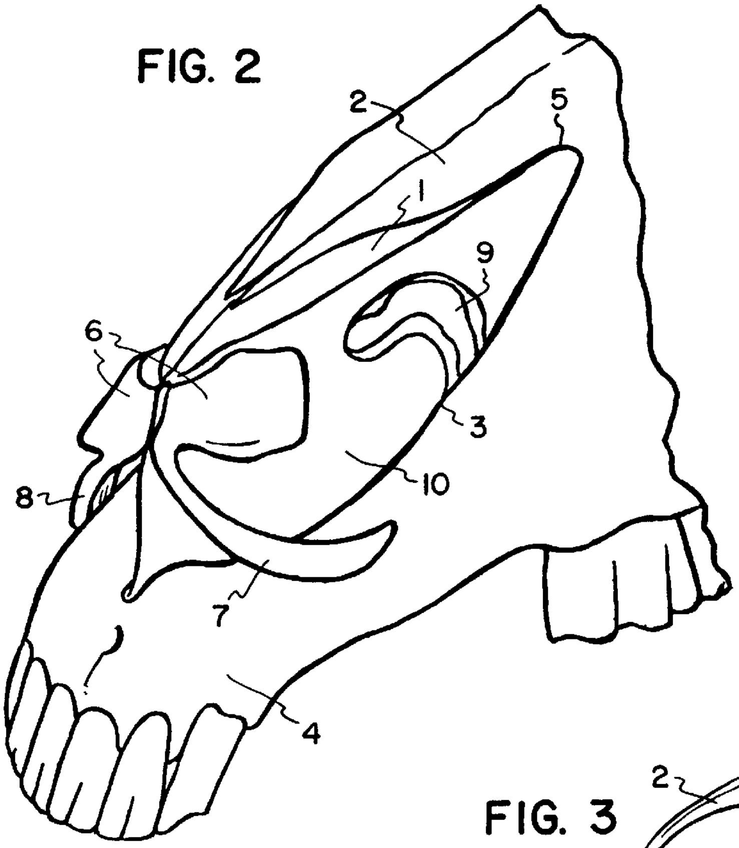
FIG. 2 is a perspective view of the bony and cartilaginous anatomy of the rostral nasal cavity of the horse.
Figure 3:
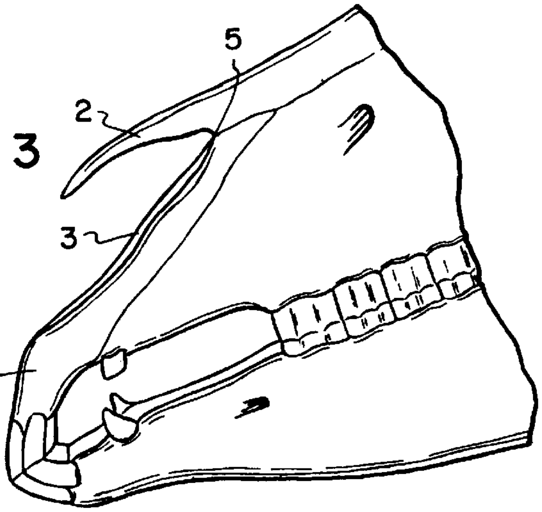
FIG. 3 is a profile view of the bony anatomy of the rostral nasal cavity of the horse.
Figure 4:
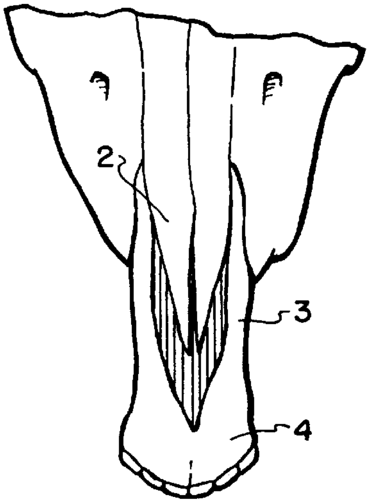
FIG. 4 is a dorsal or top view of the bony anatomy of the rostral nasal cavity of the horse.

Bony anatomical structures which surround the vestibular free wall in the horse that is supported by a device of the invention are described with reference to FIGS. 2–4. FIG. 2 is a perspective view of the bony and cartilaginous structures of the rostral nasal cavity of the horse. FIG. 3 is a profile view of the bony anatomy and FIG. 4 is a top view of the same rostral anatomy of FIG. 3. FIGS. 3 and 4 do not show cartilaginous anatomy of the adult horse.

The lateral free wall of the vestibule is defined dorsally by the dorsal lateral nasal cartilage 1 which is at the lateral most aspect of the nasal bone 2. The ventral border of the vestibular free wall is defined by the dorsal free wall 3 of the incisive bone 4. The caudal aspect of the vestibular free wall is defined by the intersection 5 of the nasal 2 and incisive 4 bones. The rostral aspect of the vestibular free wall is bordered by the nostril (not shown) which is supported dorsally by the lamina 6 and ventrally by the cornu 7 of the alar cartilage 8. The medial accessory cartilage 9 and the lamina 6 of the alar cartilage support the "false" nostril of the horse. The cartilaginous rostral nasal septum 10 is shown in FIG. 2.

Figure 5:
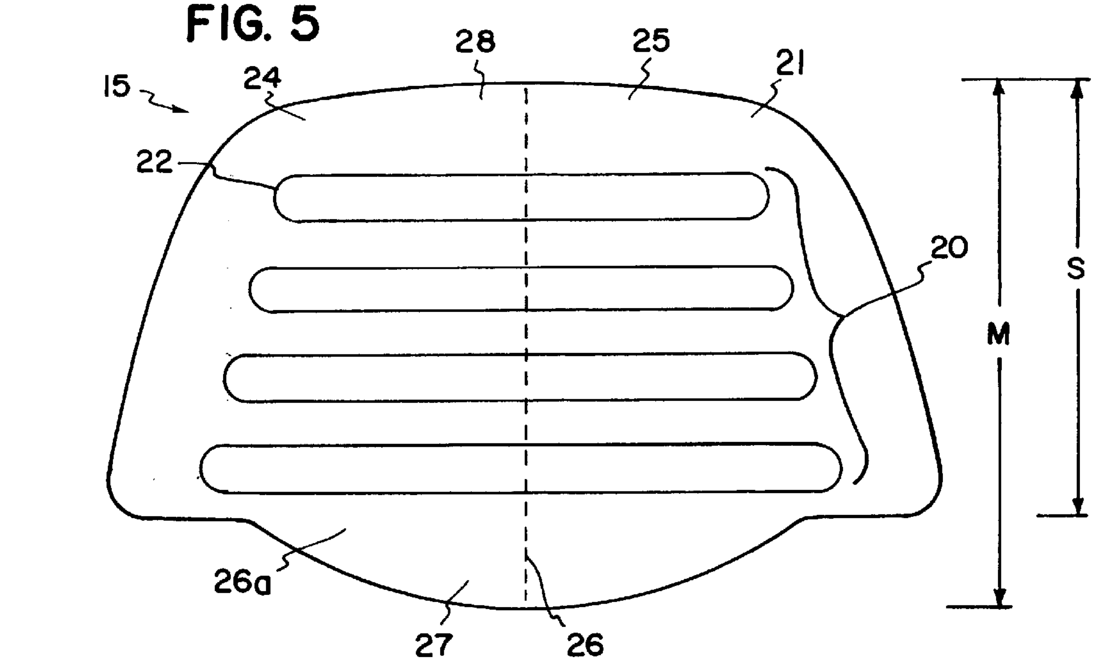
FIG. 5 is a top plan view of one embodiment of an NSD with the surface layer removed and the support layer exposed.
Figure 6:
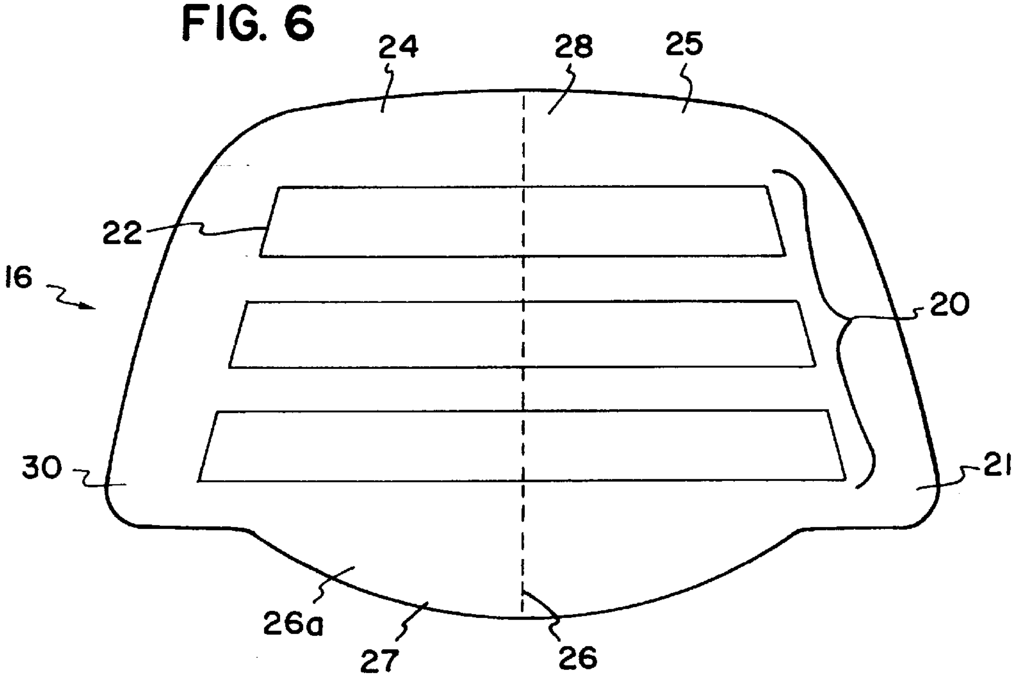
FIG. 6 is a top plan view of a second embodiment of an NSD with the surface layer removed and the support layer exposed.
Figure 7:
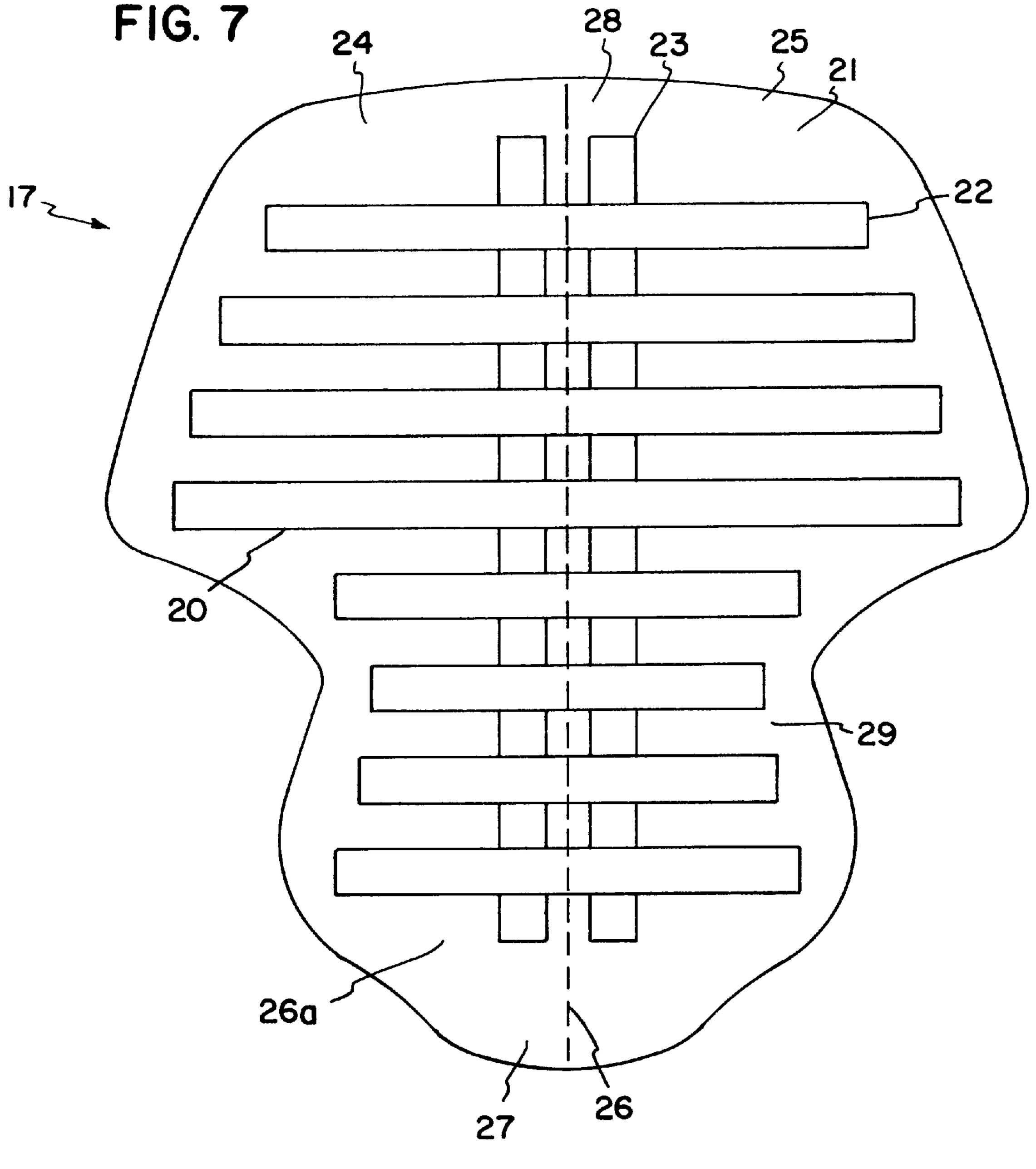
FIG. 7 is a top plan view of a third embodiment of an NSD with the surface layer removed and the support layer exposed.

FIGS. 5–7 illustrate three different embodiments of an NSD (15, 16, 17) according to the invention. The surface layer is removed in each of these figures to expose the top side of the support layer 20 and the top side of the pad layer 21 which covers the engaging layer (not shown). The support layer 20 includes transverse lift members 22 in FIGS. 5–7 and longitudinal lift members 23 in FIG. 7. The lift members 22 of FIG. 5 are narrower but greater in number than the lift members 22 of FIG. 6. In the embodiment of FIG. 2. the transverse dimension of the lift members range from 9 cm to 14 cm, the width of the transverse members is about 0.6 cm, the spacing between members is about 0.6 cm and the thickness of the lift members is about 0.14 inches. In the embodiments of FIGS. 5–7, the peripheral contours of the pad layer (and engaging layer) extend beyond the lift members.

As shown in FIGS. 5–7, an NSD includes a first side piece 24 and a second side piece 25 that intersect at the midline 26 of the midline region 26*a* of the device. In use, the rostral end 27 of the device is oriented towards the apex of the nose and the caudal end 28 of the device is oriented towards the eyes of the animal. As shown in FIG. 5, the midline rostral-poll dimension M at the midline 26 is at least equal to the side piece rostral-poll dimension S of side pieces 24 and 25. Also as shown in the embodiments of FIGS. 5–7, preferably, the rostral-poll dimension of the NSDs at the midline M are greater than the rostral-poll dimensions S of the first or second side pieces 24, 25. In FIG. 7, the NSD includes a rostrally extending center piece or "tongue" 29 that can extend rostrally to engage the nose between the nostrils.

Figure 9:
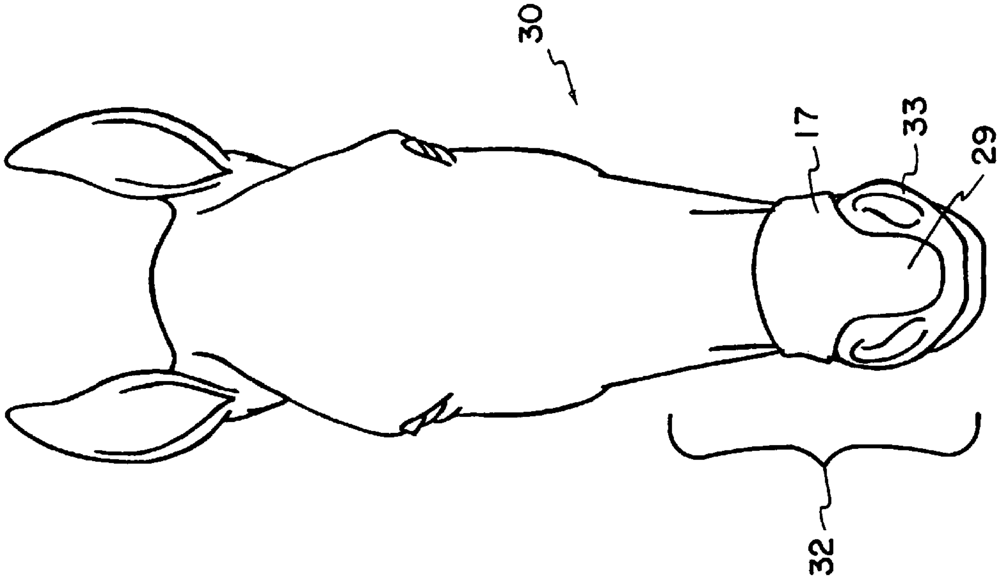
FIG. 9 is a front view of a horse having an embodiment of an NSD of FIG. 7 secured to its nose.
Figure 8:
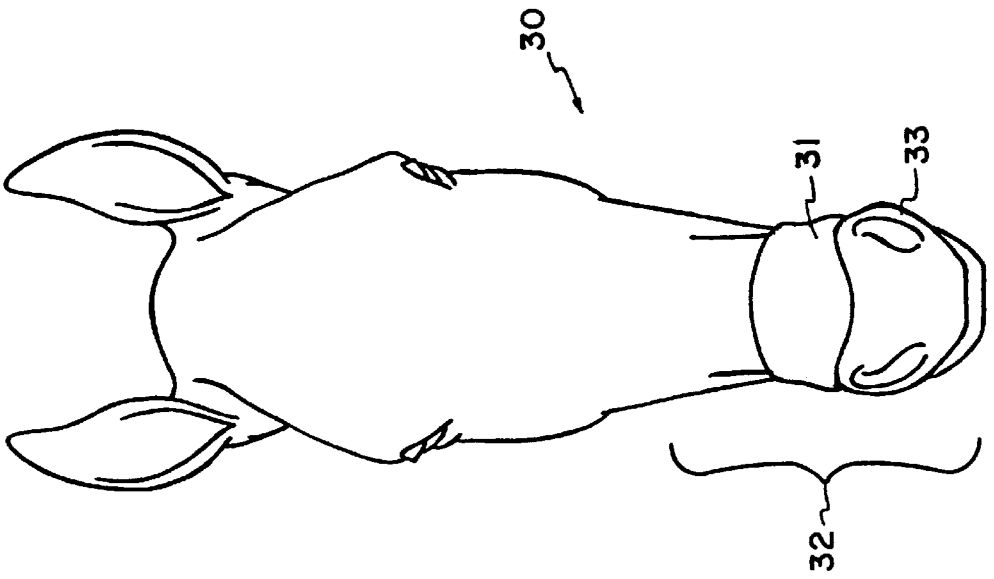
FIG. 8 is a front view of a horse having an embodiment of an NSD of FIGS. 5 or 6 secured to its nose.

In use, an NSD is secured to the animal's nose oriented generally as shown in FIGS. 8 and 9. FIG. 8 is a front view of a horse 30 having an embodiment of an NSD 31 having an external configuration as shown in FIGS. 5 and 6 (15 and 16, respectively) secured to its nose 32. FIG. 9 is a front view of a horse 30 having an embodiment of an NSD 17 as shown in FIG. 7 secured to its nose 32. As can be seen in FIG. 9, the tongue 29 of the NSD 17 extends between the nostrils 33 of the horse 30.

Figure 10:
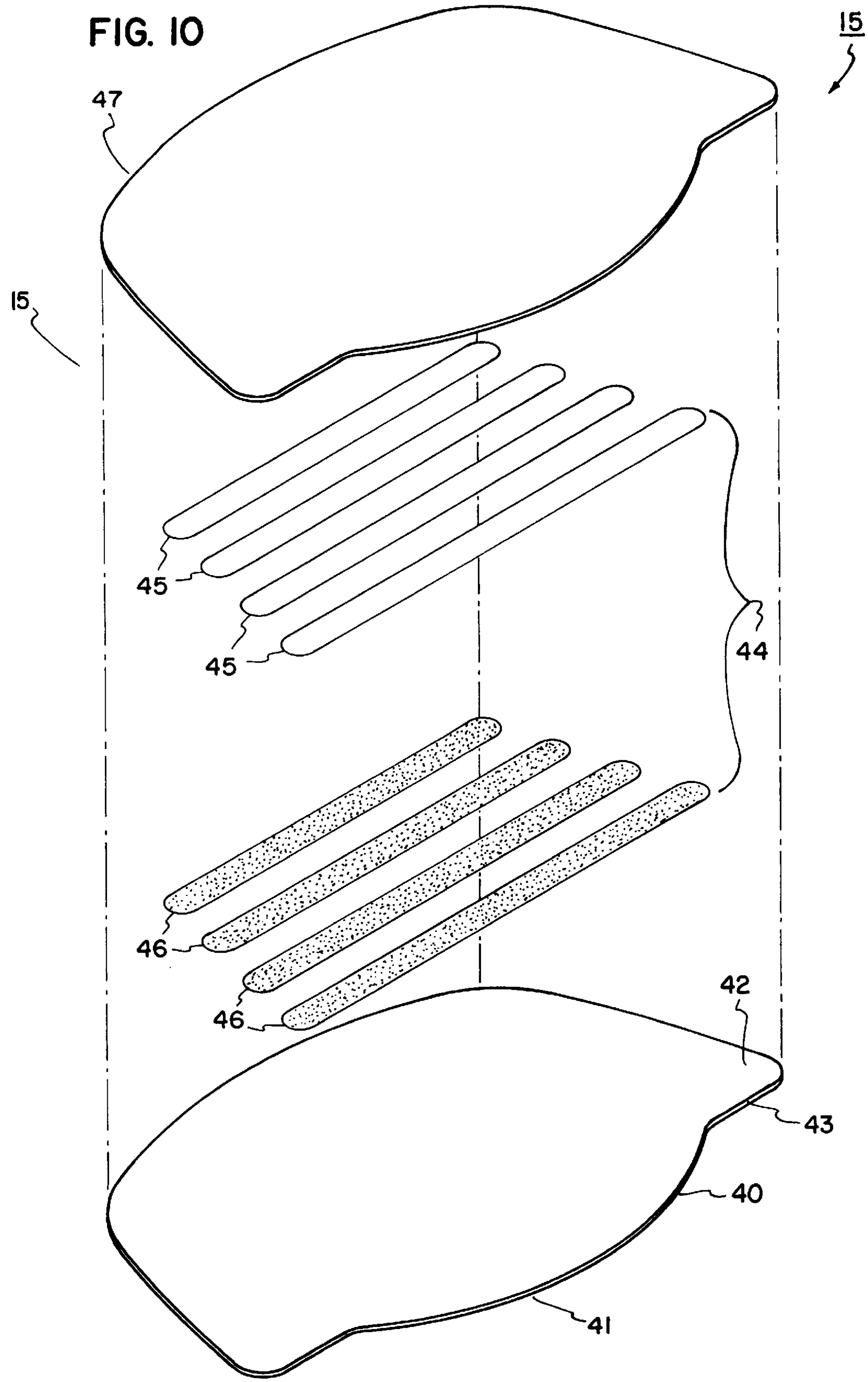
FIG. 10 is an exploded perspective view of the components of an embodiment of an NSD as shown in FIG. 5.

FIG. 10 is an exploded perspective view of the components making up an embodiment of an NSD 15 as shown in FIG. 5. According to this embodiment, the engaging layer 40 includes an adhesive surface 41 to secure the NSD 15 to an animal's nose. A pad layer 42 is adhered to the engaging layer 40. The pad layer 42 can have an adhesive layer or be adhesive free. In the embodiment shown, the engaging layer 40 is a double sided adhesive such that the top side 43 of the engaging laver will adhere to the pad layer 42. The support layer 44 includes lift members 45. The lift members 45 can be adhered to the pad layer 42 using, for example, a double sided, adhesive 46. A surface layer 47 can be applied over the support layer 44 to provide unity, additional strength or a canvas for applying an ornamental design to the device. Suitable materials for each of the layers have been described previously.

It will be apparent to one of ordinary skill in the art that many changes and modifications can be made in the invention without departing from the spirit or scope of the appended claims.

What is claimed is:

1. A nasal support device for supporting a first and second lateral vestibular wall of a nose of a horse, said device comprising:

a support layer positioned to provide support to said first and second lateral vestibular wall and comprising at least two lift members; and an engaging layer for securing said device to said nose of said horse;

said nasal support device including:

a first side piece for engaging said first lateral vestibular wall, said first side piece having a rostral end, a caudal end and a first rostral-poll dimension;

a second side piece for engaging said second lateral vestibular wall, said second side piece having a rostral end, a caudal end and a second rostral-poll dimension;

a midline region including an intersection of said first and second side pieces, said midline region having a rostral end, a caudal end and a midline region rostral-poll dimension of about 5–18 cm, said midline region rostral poll dimension being at least as great as a selected one of said first rostral-poll dimension and said second rostral poll dimension;

a transverse dimension defined by a length of said nasal support device extending from a peripheral edge of said first side piece to a peripheral edge of said second side piece, wherein said transverse dimension is about 10 cm to about 17 cm.

2. A nasal support device according to claim 1 wherein when secured to said nose of said horse said rostral end of said midline region extends rostrally between a first and second nostril of said horse.

3. A nasal support device according to claim 1 wherein said first and second side pieces include one or more lift members which traverse a rostral-poll dimension of said vestibular wall.

4. A nasal support device according to claim 1 wherein when secured to said nose of said horse said first and second side pieces are configured to extend to an incisive bone of said horse.

5. The nasal support device according to claim 1 wherein said midline region rostral-poll dimension is greater than said selected one of said first and second rostral-poll dimension.

6. A nasal support device according to claim 1 wherein said support layer of said nasal support device includes three lift members.

7. A nasal support device according to claim 6 comprising a surface layer attached to said support layer.

8. A nasal support device according to claim 1 wherein when secured to said nose said first and second side pieces are configured to extend over a portion of said vestibular wall of said horse.

9. A nasal support device according to claim 1 wherein said horse for which said nasal support device is sized is an adult horse.

10. A nasal support device according to claim 9 wherein said rostral-poll midline dimension is about 5 to 18 cm and said first and second side pieces each have a rostral-poll dimension of about 5 to 8 cm.

11. A nasal support device according to claim 1 wherein said horse for which said nasal support device is sized is a foal.

12. A nasal support device according to claim 1 wherein said lift members have a length of about 4 to 18 cm.

13. A nasal support device according to claim 12 wherein said lift members have a width of about 0.2 to 2 cm.

14. A nasal support device according to claim 12 wherein said lift members have a space therebetween of about 0.2 to 2 cm.

15. A nasal support device according to claim 1 wherein each of said lift members have a length of about 4–18 cm, a width of about 0.2 to 2 cm and a spacing between said lift members of about 0.2 to 2 cm.

16. A nasal support device according to claim 1 wherein said lift members have a thickness of about 0.008 to 0.20 inches.

17. A nasal support device according to claim 1 wherein said engaging layer is a double-sided adhesive which extends beyond a periphery of said support layer.

18. A nasal support device according to claim 1 wherein said lift members are a thermoplastic resin.

* * * * *